(12) United States Patent
Bewlay et al.

(10) Patent No.: US 6,393,916 B1
(45) Date of Patent: May 28, 2002

(54) ULTRASONIC INSPECTION METHOD AND SYSTEM

(75) Inventors: Bernard Patrick Bewlay, Schenectady; John Broddus Deaton, Jr., Niskayuna; Michael Francis Xavier Gigliotti, Jr., Scotia; Robert Snee Gilmore, Charlton, all of NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/454,191

(22) Filed: Dec. 3, 1999

(51) Int. Cl.⁷ .............................................. G01N 29/00
(52) U.S. Cl. ............................. 73/606; 73/597; 73/598; 73/602; 73/627
(58) Field of Search .......................... 73/606, 613, 620, 73/627, 644, 624, 579, 597, 598, 622, 628, 641, 642; 310/313 R; 148/699, 671; 29/527.5

(56) References Cited

U.S. PATENT DOCUMENTS

| | | | | |
|---|---|---|---|---|
| 3,981,184 A | * | 9/1976 | Matay | 73/609 |
| 4,187,725 A | * | 2/1980 | Gavrev et al. | 73/613 |
| 4,313,070 A | * | 1/1982 | Fisher | 73/627 |
| 4,539,848 A | * | 9/1985 | Takafuji et al. | 73/599 |
| 5,026,520 A | * | 6/1991 | Bhowal et al. | 420/417 |
| 5,277,718 A | * | 1/1994 | Paxson et al. | 148/671 |
| 5,442,847 A | * | 8/1995 | Semiatin et al. | 29/527 |
| 5,533,401 A | * | 7/1996 | Gilmore | 73/622 |
| 5,767,408 A | * | 6/1998 | Lindgren et al. | 73/597 |
| 5,894,092 A | * | 4/1999 | Lindgren et al. | 73/598 |
| 6,202,489 B1 | * | 3/2001 | Beffy et al. | 73/598 |

OTHER PUBLICATIONS

The Journal of The Acoustical Society of America, Revised Grain–Scattering Formulas and Tables, Emmanuel P. Papadakis, vol. 37, No. 4, pp. 703–710, Apr. 1965.
The Journal of The Acoustical Society of America, Ultrasonic Attenuation Caused by Scattering in Polycrystalline Metals, Emmanuel P. Papadakis, vol. 37, No. 4, pp. 711–717, Apr. 1965.

* cited by examiner

*Primary Examiner*—Hezron Williams
*Assistant Examiner*—Jacques Saint-Surin
(74) *Attorney, Agent, or Firm*—Robert P. Santandrea; Noreen C. Johnson

(57) ABSTRACT

An ultrasonic inspection method for determining acceptability of material for microstructurally sensitive applications comprises providing a material, directing ultrasonic energy of ultrasonic inspection to the material; scattering reflected energy in the material; determining an amount of noise generated by the ultrasonic inspection; and characterizing the material as acceptable if the amount of noise corresponds to a pre-determined noise level. The invention also sets forth a system for implementing the method, as embodied by the invention.

32 Claims, 8 Drawing Sheets

(a)
 (b)
 (c)
 (d)

ULTRASONIC INSPECTION METHOD AND SYSTEM

BACKGROUND OF THE INVENTION

The invention relates to titanium inspection methods and systems. In particular, the invention relates to methods and systems for inspecting titanium using ultrasonic energy.

Nondestructive evaluation by ultrasonic inspection and ultrasonic inspection testing is a known material testing and evaluation method. Ultrasonic testing typically requires that detectable flaws possess different acoustic behaviors from bulk material under similar ultrasonic inspection. This different behavior permits the ultrasonic inspection technique to detect flaws, grains, imperfections, and other related microstructural characteristics for a material.

Materials with large, elastically anisotropic grains, such as, but not limited to, cast ingots of steels, titanium alloys, and nickel alloys, are often difficult to evaluate by ultrasonic testing. The difficulties arise, at least in part to, because sound waves, which are used for ultrasonic inspection, can be partially reflected from grains, and represent a background "noise." The generated background noise can mask flaws in the material, and is thus undesirable.

Ultrasonic inspection techniques have been developed that use focused ultrasonic beams to enhance a flaw fraction within any instantaneously insonified volume of material. These developed ultrasonic inspection techniques can identify indications based both on maximum signal, as well as signal to noise. A scattering of sound in a polycrystalline metallic material body, which is also known in the art as an attenuation of a propagating sound wave, can be described as a function of at least one of the following: grain dimensions, intrinsic material characteristics, and ultrasound frequency. Typically, three different functional relationships among scattering, frequency, and grain dimensions have been described. These are:

for $\lambda > 2\pi D$, $a = T v^4 \Theta$, termed "Rayleigh" scattering;

for $\lambda < 2\pi D$ or $\lambda = D$, $a = D v^2 \Sigma$, termed "stochastic" or "phase" scattering; and for $\lambda << D$, a 1/D, termed "diffusion" scattering;

where a is attenuation, $\lambda$ is wavelength of the ultrasound energy, v is frequency of the ultrasound energy, D is an average grain diameter, T is a scattering volume of grains, and $\Theta$ and $\Sigma$ are scattering factors based on elastic properties of the material being inspected.

The microstructure of a material can determine the applications in which the material can be used, and the microstructure of a material can limit the applications in which the material can be used. The microstructure can be determined by measuring the scattering of sound waves in a material. The scattering of sound in a material, such as titanium, is sensitive to its microstructure. The titanium microstructure's sound scattering sensitivity can be attributed to $\alpha$Ti particles that are arranged into "colonies." These colonies typically have a common crystallographic (and elastic) orientation, and these colonies of $\alpha$Ti particles can behave as large grains in the titanium material. An individual $\alpha$Ti particle might be about 5 $\mu$m in diameter, however, a colony of $\alpha$Ti particles could be greater than about 200 $\mu$m in diameter. Thus, the size contribution attributed to sound scattering sensitivity from $\alpha$Ti particles could vary over 40-fold among differing microstructures. Additionally, the sound scattering sensitivity due to $\alpha$Ti particles could change between that from randomly oriented $\alpha$Ti particles to that from $\alpha$Ti particles within oriented colonies of $\alpha$Ti particles.

Colony structures are formed during cooling a titanium alloy from a high temperature as $\beta$Ti transforms to $\alpha$Ti.

There is a crystallographic relation between the $\alpha$Ti and the parent $\beta$Ti grain, such that there are only three crystallographic orientations that $\alpha$Ti will take when forming from a given $\beta$Ti grain. If the cooling rate is high and there is uniform nucleation of $\alpha$Ti throughout the grain, neighboring $\alpha$Ti particles have different crystallographic orientations, and each behave as distinct acoustic scattering entities. However, if there are only a few sites of $\alpha$Ti nucleation within the $\beta$Ti grain, then the $\alpha$Ti particles in a given area all grow with the same crystallographic orientation, and a colony structure results. This colony becomes the acoustic entity. Since a colony is formed within a $\beta$Ti grain, the colony size will be less than the $\beta$Ti grain size. The size of $\beta$Ti grains and the nature of $\alpha$Ti particles colony structures are important variables that influence ultrasonic noise and ultrasonic inspection in single phase and two-phase titanium alloys and materials. Therefore, the size of $\beta$Ti grains and the nature of $\alpha$Ti particles in colony structures may influence ultrasonic inspection techniques, methods, and results by creating undesirable noise during ultrasonic inspection. While thermomechanical processing techniques, which rely on dynamic recrystallization in the $\alpha+\beta$ temperature range to achieve uniform fine grain (UFG) $\alpha$Ti particles and prevent colony formation, have been developed to improve titanium microstructure, defects may remain in the titanium material. These defects may be undesirable for some titanium material applications.

Thus, in order to have acceptable titanium for certain applications, it is desirable to provide an ultrasonic inspection process that accurately determines the nature of noise during ultrasonic inspection. The ultrasonic inspection method should determine if ultrasonic noise is attributed to a defect in the titanium material, or is due to other factors.

Therefore, a need exists for an ultrasonic inspection method for determining material characteristics and properties. Further, a need exists for an ultrasonic inspection method for determining processed titanium characteristics and properties. Furthermore, a need exists determining material configurations and characteristics for accurate ultrasonic inspection methods.

SUMMARY OF THE INVENTION

In one aspect of the invention, an ultrasonic inspection method for determining acceptability of material for microstructurally sensitive applications is provided. The method comprises providing a material, directing ultrasonic energy of ultrasonic inspection to the material; scattering reflected energy in the material; determining an amount of noise generated by the ultrasonic inspection; and characterizing the material as acceptable if the amount of noise corresponds to a preset noise level.

In another aspect of the invention, a system for implementing the method, as embodied by the invention is provided. The ultrasonic inspection system for determining acceptability of material for microstructurally sensitive applications comprises means for providing a material, means for directing ultrasonic energy of ultrasonic inspection to the material; means for scattering reflected energy in the material; means for determining an amount of noise generated by the ultrasonic inspection; and means for characterizing the material as acceptable if the amount of noise corresponds to a preset noise level.

These and other aspects, advantages and salient features of the invention will become apparent from the following detailed description, which, when taken in conjunction with the annexed drawings, where like parts are designated by like reference characters throughout the drawings, disclose embodiments of the invention.

DESCRIPTION OF THE INVENTION

Figure 1:
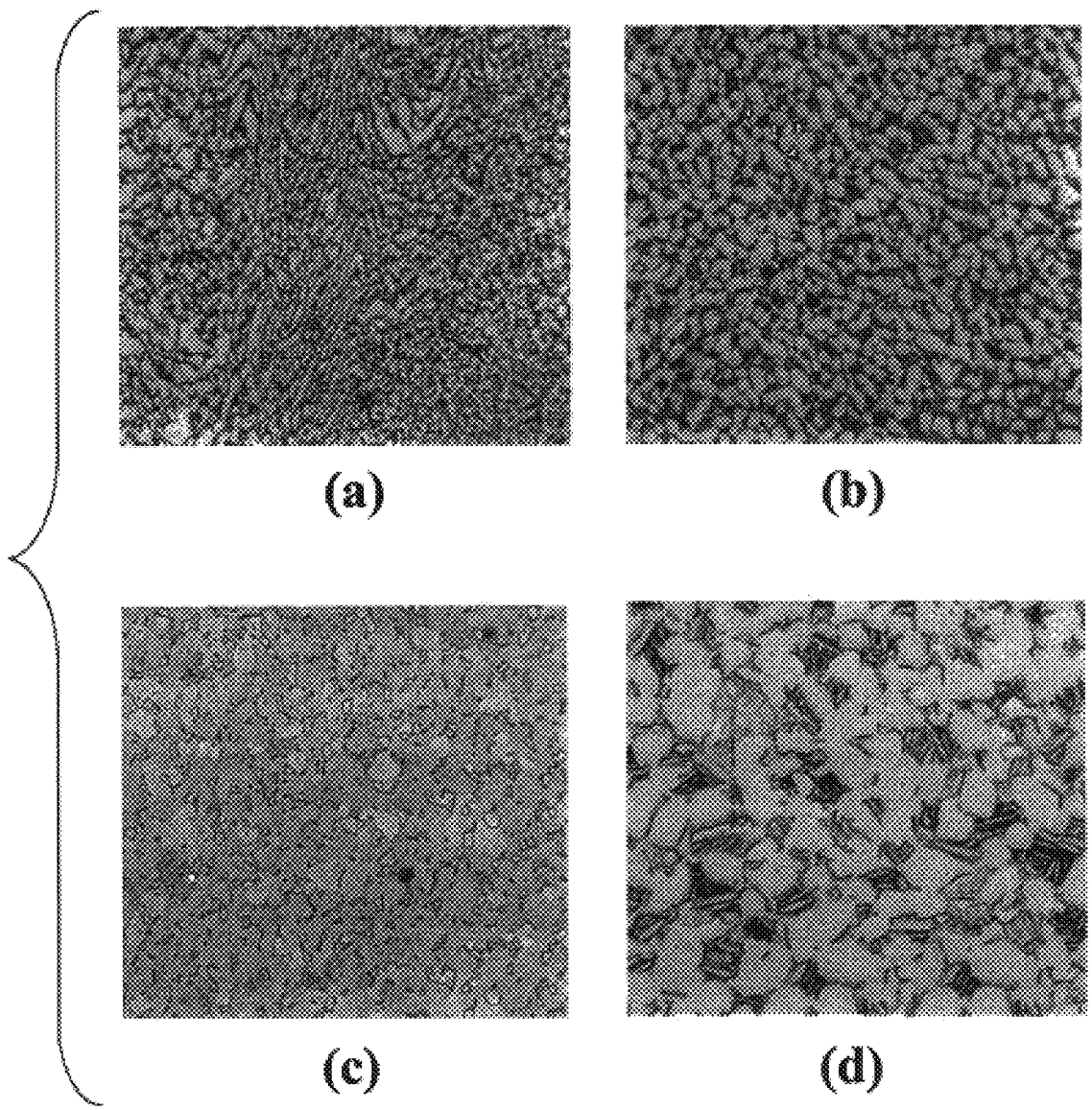
FIG. 1 illustrates light micrographs of Ti6242 material that in the following conditions: (a) conventional billet; (b) conventional forging; (c) uniform fine grain (UFG) billet; (d) a forging of a UFG billet.

The ultrasonic inspection methods and systems, as embodied by the invention, determine that microstructures of uniform-fine grain (UFG) billets and forgings made from UFG billets comprise fine-scale granular αTi particles. Also, the ultrasonic inspection indicates that uniform-fine grain (UFG) billets and forgings made from UFG billets, and the inspectability of articles comprising the microstructures of uniform-fine grain (UFG) billets and forgings made from UFG billets, generally produces predominantly Rayleigh scattering, which means that the Rayleigh scattering comprises at least a majority of the scattering and dominates other types of scattering. Thus, as embodied by the invention, the ultrasonic inspection to determine if the titanium-containing materials comprise uniform-fine grains are suitable for various microstructurally sensitive applications, is enhanced since microstructures of predominantly Rayleigh scattering (UFG) billets and forgings made from UFG billets generate predominantly Rayleigh scattering. If the ultrasonic inspection, as embodied by the invention, determines scattering other than predominantly Rayleigh scattering, for example phase scattering alone or in combination with Rayleigh scattering, it is possible to characterize the material as not being uniform-fine grain titanium.

αTi particles are generally less than about 5 μm in diameter, and are generally formed with an absence of crystallographic texture. The ultrasonic inspectability of these UFG titanium materials is characterized by a signal to noise ratio from machined flat bottom holes. The signal to noise ratio obtained by ultrasonic inspection, as embodied by the invention, is greater in UFG titanium materials than in the conventional titanium materials. It has been determined that there is less ultrasonic backscattered noise in the UFG titanium materials than in the conventional titanium materials. Further, it has been determined using ultrasonic inspection, as embodied by the invention, that an ultrasonic signal from machined flat bottomed holes is higher in the UFG titanium material.

Further, the ultrasonic inspection, as embodied by the invention, indicates that the presence of a αTi particle colony structure is associated with ultrasonic noise. For titanium materials with αTi particles less than about 10 μm in size, differences in αTi particle size typically do not have a significant effect on generated ultrasonic noise. For example, UFG billets display chiefly Rayleigh scattering, while conventional billets, which are not be characterized by UFG properties, display Rayleigh scattering plus phase scattering when subjected to ultrasonic inspection, as embodied by the invention. Therefore, as embodied by the invention, the inspectability of titanium-containing materials is enhanced when there is predominantly Rayleigh scattering.

The ultrasonic inspection method, as embodied by the invention, involves determining microstructural characteristics and features of a material using the material's sound scattering sensitivity. The ultrasonic inspection method comprises providing a material, for example titanium. The ultrasonic inspection, as embodied by the invention, will be described with reference to the titanium material comprising a Ti6242 alloy, however, this material is merely exemplary of the titanium materials within the scope of the invention. The description of a Ti6242 alloy is in no way intended to limit the scope of the invention. The titanium material is then subjected to ultrasonic inspection, as embodied by the invention, by directing ultrasonic energy onto the titanium material. The ultrasonic energy directed into the material is typically a pulse of sound of a selected frequency. The sound pulse is scattered in a manner determined by the frequency of the sound pulse, the microstructural features of the titanium material, and by intrinsic physical characteristics—elastic constants and mass density—of the titanium material. The scattered energy is then analyzed and a determination of the characteristics of the scattered noise is made with regard to the nature of the scattering.

The invention is also directed to a system that is capable of implementing the ultrasonic inspection method, in which the invention comprises apparatus, sensors, ultrasonic inspection apparatus, and other means for implementing the invention. For example, and in no way limiting of the invention, the system includes at least one control structure that may comprise any appropriate high-powered solid-state switching device. The control may be a computer. However, this is merely exemplary of an appropriate high-powered control, which is within the scope of the invention. For example but not limiting of the invention, the control for the ultrasonic inspection can comprise at least one of a silicon controlled rectifier (SCR), a thyristor, MOS-controlled thyristor (MCT) and an insulated gate bipolar transistor. The control can be implemented as a single special purpose integrated circuit, such as ASIC, having a main or central processor section for overall, system-level control, and separate sections dedicated performing various different specific combinations, functions and other processes under control of the central processor section. It will be appreciated by those skilled in the art that the control can also be implemented using a variety of separate dedicated or programmable integrated or other electronic circuits or devices, such as hardwired electronic or logic circuits including discrete element circuits or programmable logic devices, such as PLDs, PALs, PLAs or the like. The control can also be implemented using a suitably programmed general-purpose computer, such as a microprocessor or microcontrol, or other processor device, such as a CPU or CPU, either alone or in conjunction with one or more peripheral data and signal processing devices.

The titanium material for ultrasonic inspection, as embodied by the invention, comprises a uniform fine grain (UFG) material. The UFG titanium can be produced by forging a billet of conventional titanium material into various and appropriate structures, configurations, and shapes. For example, the UFG titanium for ultrasonic inspection, as embodied by the invention, can be formed by the steps of press forging, heat-treating, quenching, and subsequent cooling. The titanium that is actually subjected to the ultrasonic inspection, as embodied by the invention, may be further prepared by providing a titanium billet with at least one, for example a series, of flat bottom holes. These flat bottom holes will serve as pixel intensity standards, upon which the ultrasonic inspection can be gauged.

A signal to noise ratio for synthetic flaws machined in the Ti6242 blocks is strongly influenced by microstructural condition, for example as the Ti6242 is measured by electron backscatter diffraction analysis. Ti6242 blocks having a microstructure comprising uniform, fine, texture-free αTi particles typically provided signal to noise ratios about 20 dB greater than similar titanium blocks with microstructures having colonies comprising crystallographically aligned αTi particles.

The ultrasonic inspection method and procedure, as embodied by the invention, will now be described with reference to specific materials for exemplary purposes. The following discussion is merely exemplary and is not intended to limit the invention in any manner. In the following discussion, the terms are used with their normal meanings as understood by person of ordinary skill in the art, unless discussed to the contrary. Further, the dimensions are approximate, unless stated to be exact.

The ultrasonic inspection provides Ti6242 for evaluation. The Ti6242 is evaluated under four microstructural conditions: a conventional billet; a conventional forging from conventional billet; a uniform fine grain (UFG) billet; and a forging of the UFG billet. The individual billets will be referred to by the above names, and collectively as "billets".

The conventional billet is about 23 centimeters (cm) (9 inch) in diameter. The conventional forging is from the bore region of a disk forging, for example a compressor disk forging. The UFG billet is produced as two bars from about 10 cm×10 cm×20 cm sections taken from the commercial billet and having its grain refined under accepted titanium alloy grain refinement processes. The forging of UFG billet is produced by press forging at temperatures of about 900° C. about a 7 cm tall, 6.35 cm diameter cylinder of the UFG billet to about a 2.80 cm final height at 2.5 cn/min pressing speed. The forging of UFG billet is given a heat treatment of about 970° C., for about 1 hour, followed by a helium quench, at about 705° C., for about 8 hours, followed by an air cool.

Figure 2:
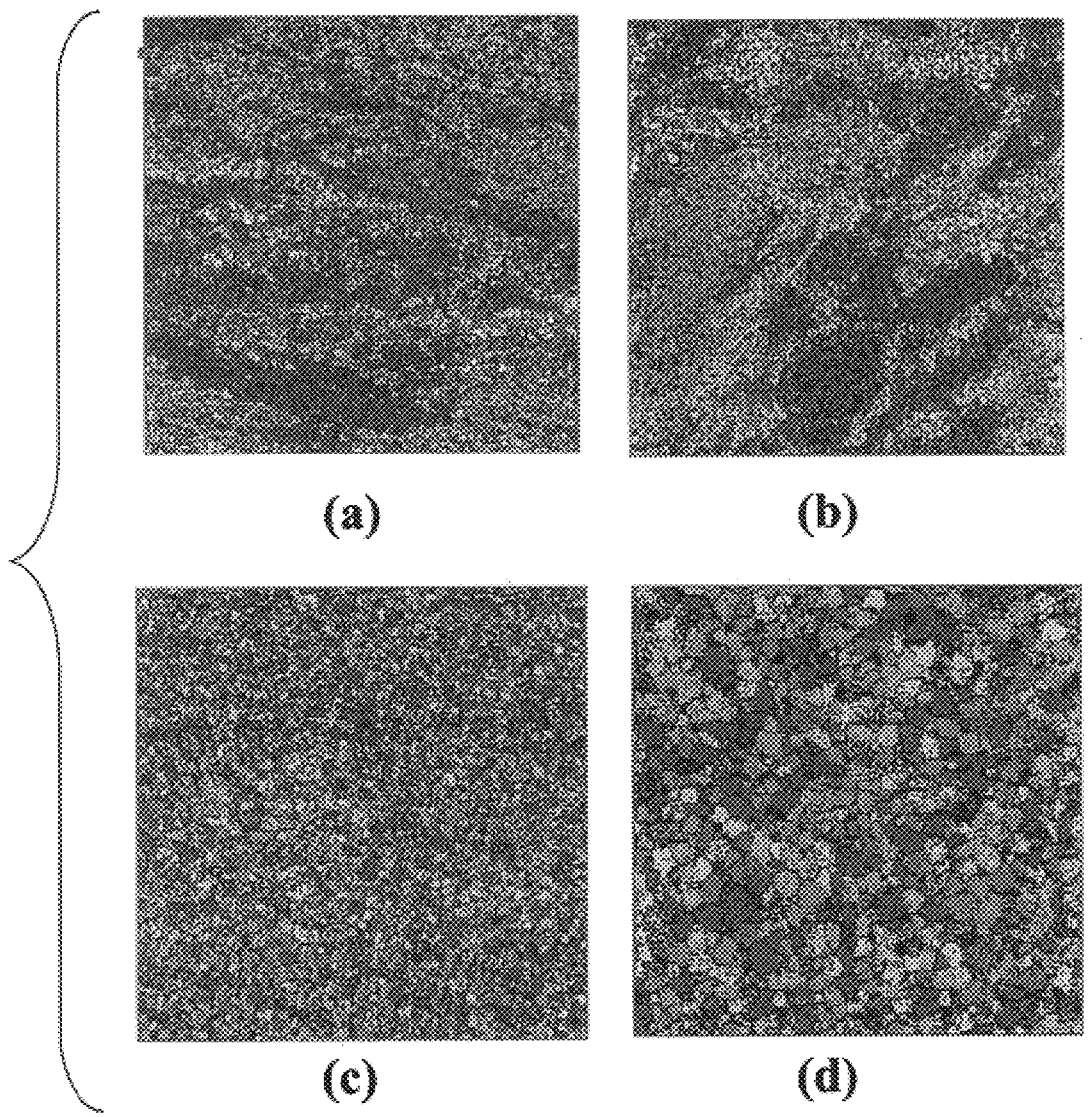
FIG. 2 illustrates icosahedral images generated from EBSP analysis of a Ti6242 material in the following conditions: (a) conventional billet; (b) conventional forging; (c) UFG billet; (d) forged UFG billet.
Figure 3:
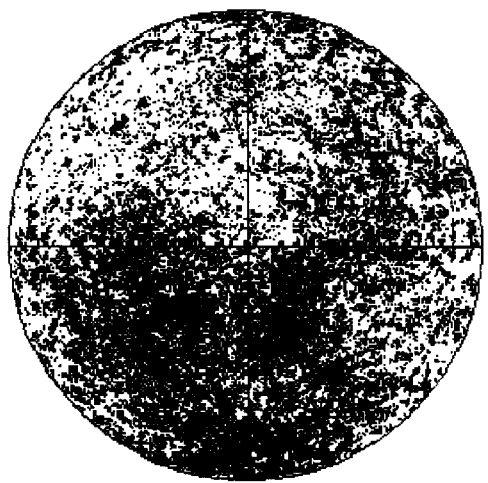
FIG. 3 illustrate [0001] pole figures generated from EBSP analysis of a Ti6242 material in the following conditions: (a) conventional billet; (b) conventional forging; (c) UFG billet; (d) forged UFG billet.
Figure 3:
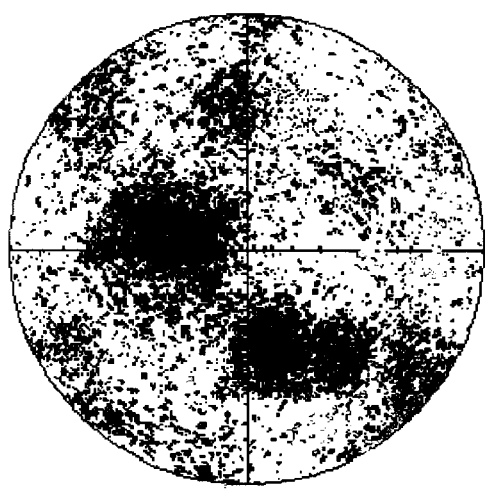
Figure 3:
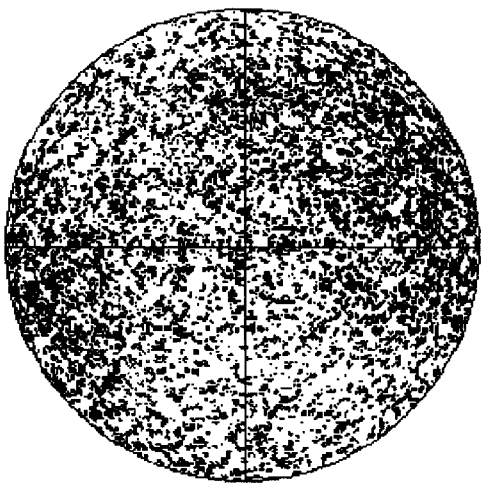
Figure 3:
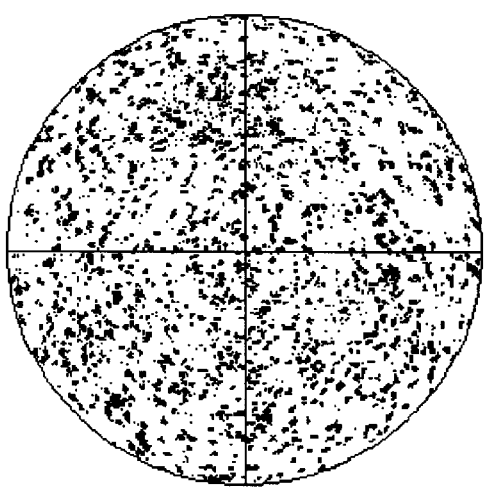

The microstructure of each billet is then evaluated by light microscopy. The crystallographic texture of each billet is then determined by electron backscatter diffraction pattern (EBSP) analysis. Light micrographs for each billet are displayed in FIG. 1, where legend (a) is the conventional billet; legend (b) is the conventional forging; legend (c) is the UFG billet; and legend (d) is the forged UFG billet. FIG. 2 shows EBSP "icosohedral" images, in which the [0001] pole inclination of a scanned microstructure is represented in colors. In FIG. 2, colors that are close to one another on an accepted "20-sided (icosahedral) color sphere" represent microstructure inclinations that are similar in pole inclination. Further, in FIG. 2, a black pixel is a pixel for which no crystallographic orientation can be determined. Further, FIG. 3 shows [0001] pole figures for the regions of the scanned images FIG. 2. The legends for FIGS. 2 and 3 are similar to those of FIG. 1.

As illustrated, the conventional billet microstructure contains primary αTi plates, with a thickness of about 5 $\mu$pm, and lengths in a range from about 5 $\mu$m to about 10 $\mu$m, as illustrated in FIG. 1 legend (a). The αTi plates are arranged in colonies, typically about 100 $\mu$m wide and over about 300 $\mu$m long, as illustrated in FIG. 2 legend (a). The αTi phase crystallographic orientation of the sample scanned in FIG. 2 legend (a) indicate strong crystallographic texture, with most [0001] poles in the lower region of the pole, as illustrated in FIG. 3 legend (a).

The microstructure of the forging from the conventional billet contains primary αTi particles, with diameters in a range from about 5 to about 10 $\mu$m, FIG. 1 legend (b). As illustrated, there appears to be substantial breakup of the billet microstructure. αTi particles are arranged in large colonies comprising similar crystallographic orientations. For example, some αti colonies are about 300 $\mu$m wide and often greater than about 1000 $\mu$m long, as illustrated in FIG. 2, legend (b). The αTi phase crystallographic orientation of the sample scanned in FIG. 2, legend (b) has strong crystallographic texture, meaning that a majority of the [0001] poles are grouped within two regions of the pole figure, as illustrated in FIG. 3, legend (b). This strong grouping of the poles suggests that the scanned region comprises two colonies.

The ultrasonic inspection of the UFG billet indicates a microstructure comprising αTi particles. The particles comprise diameters about 5 $\mu$m, as illustrated in FIG. 1, legend (c). These αTi particles do not appear to be provided in colonies, as illustrated in FIG. 2, legend (c). The αTi phase orientation of the sample scanned as illustrated in FIG. 2, legend (c) appears random, as illustrated in FIG. 3, legend (c).

The microstructure of the heat-treated forging of the UFG billet indicates that it comprises αTi particles. The αTi particles have diameters about 10 $\mu$m, as illustrated in FIG. 1, legend (d). These αTi particles in the forging are larger than those in the billet from which the forging was made, and this suggests grain growth during at least one of forging or heat treatment of the UFG billet. The αTi particles are not provided in colonies, as illustrated in FIG. 2, legend (d). The αTi phase crystallographic orientation appears random, as illustrated in FIG. 3, legend (d).

The ultrasonic characteristics, as embodied by the invention, of the billets formed different materials are determined by C-scans of blocks formed from billets of the titanium-containing materials. The blocks are provided with 0.79 mm (1/32 inch) diameter flat bottom holes. The blocks are formed about 38 mm thick with holes drilled to about 25 mm below top surface of the block. Each of the conventional billet, conventional forging, and UFG billet have surface dimensions about 64 millimeters (mm) square, and each also has 9 flat bottom holes. The forging made from the UFG material had dimensions about 64 mm by about 28 mm, and is provided with 6 flat bottom holes. Each block is machined with sufficient orientations so that an ultrasonic inspection direction is similar to that of a larger component formed from the titanium-containing material. For example, the 38 mm thickness of the block is disposed in the radial direction of the billet or forging.

The ultrasonic transducers used for the ultrasonic inspection by C-scanning processes are listed in Table 1. Table 1 also provides characteristics of the ultrasonic transducers. The transducers comprise polyvinylidine fluoride (PVDF) as a piezoelectric element. Center frequencies for the ultrasonic transducers are measured from signals reflected off the backwall of a fused silica block.

TABLE 1

Characteristics of Transducers

| Transducer | Nominal Frequency | Actual Frequency | Diameter | Focal Length | Aperture |
|---|---|---|---|---|---|
| 1 | 5 MHz | 6.62 MHz | 19 mm | 133 mm | f/7 |
| 2 | 10 MHz | 11.36 MHz | 19 mm | 133 mm | f/7 |
| 3 | 20 MHz | 18.43 MHz | 19 mm | 133 mm | f/7 |

Two separate series of water immersion ultrasonic C-scans were performed on the titanium-containing blocks. The series of water immersion ultrasonic C-scans were performed at nominal frequencies of about 5 MHz, about 10 MHz, and 20 MHz. One scan at each of the above-frequencies is performed to measure a signal from the flat bottom holes. A second scan at each of the above-frequencies is performed at a higher amplification to get noise and sound scattering sensitivity statistics.

Each of the scans is made over a square region about 147.5 mm in length and width, with about a 0.144 mm scan and index increment. The sound is focused about 25 mm below the top surface of the blocks, which is disposed in the approximate the plane of the flat bottom holes. The width of scan signal gate is about 4 microseconds. The obtained C-scan images are about 1024 pixels by about 1024 pixels.

Figure 4:
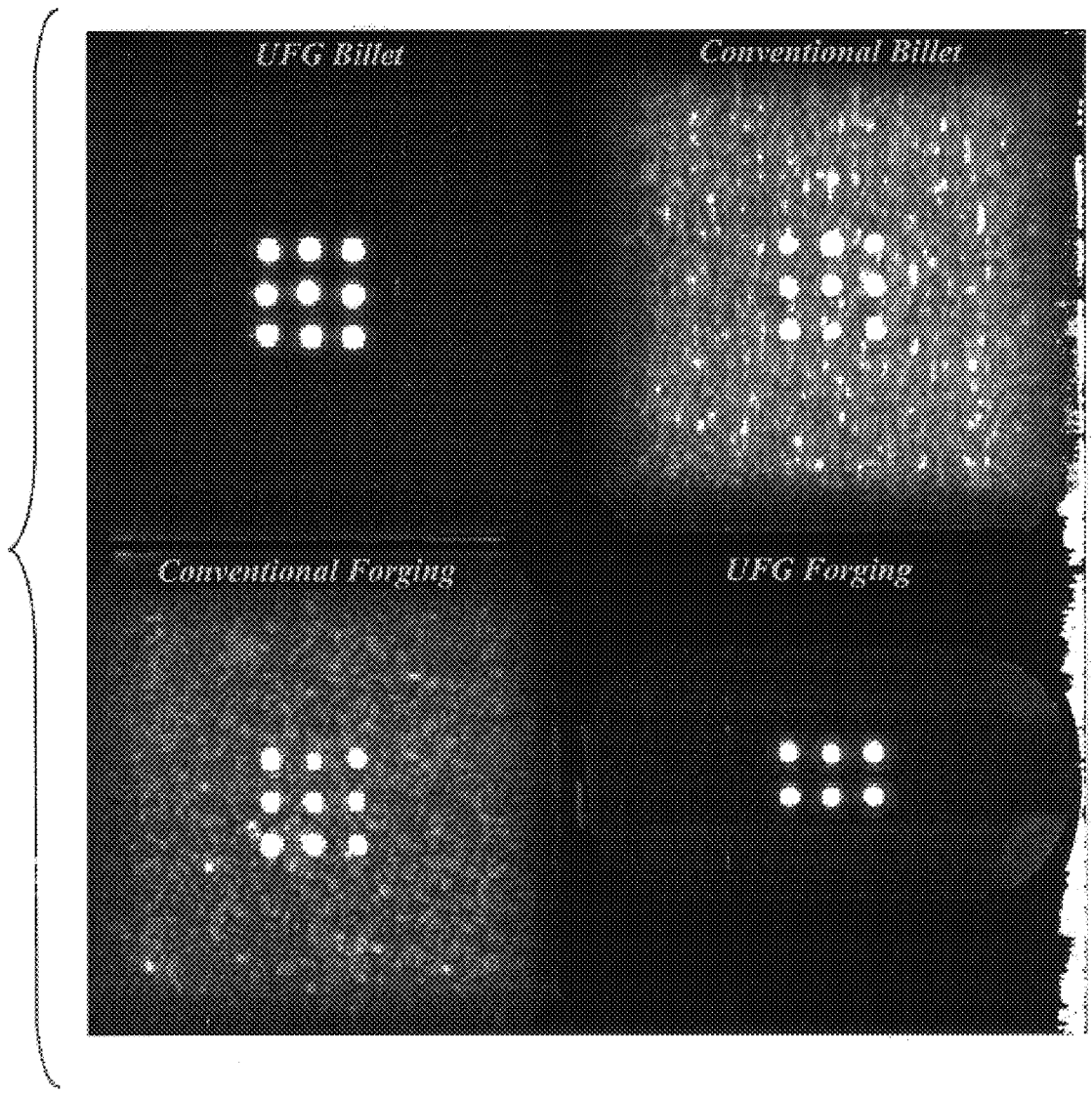
FIG. 4 illustrate 5 MHz C-scan images of Ti6242 blocks containing arrays of 0.79 mm (1/32 inch) diameter flat bottom holes, which are drilled 25 mm below a surface, in which the top left is titanium UFG billet, the top right is a conventional titanium billet, the bottom left is a conventional titanium forging, and the bottom right is a titanium UFG forging, wherein the 5 MHz C-scan images are taken at 12 dB attenuation noise scan.

FIG. 4, legends a–d, illustrate C-scan images made at about 5 MHz. With reference to FIG. 4, the UFG billet material is in the upper left, the conventional billet is on the upper right, the conventional forging is on the lower left, and the forging of the UFG material is on the lower right. The conventional billet and forging exhibit a higher background noise, as indicated by brighter pixels in those blocks as illustrated in FIG. 4, legend (a). A lower intensity is exhibited from the flat bottom holes, as indicated by a lower intensity of pixels from those regions as illustrated in FIG. 4, legend (b).

Quantitative measures of signal and noise can then be determined from the C-scans. The signal from each flat bottom hole is taken as the brightest pixel within the 3×3 array of the nine brightest pixels. Noise statistics and sound scattering sensitivity can then be determined from square pixel arrays that did not comprise the flat bottom holes. The quantitative data is presented in Table 2. In Table 2, a signal is an average signal from all flat bottom holes in the respective block. The signal to noise ratios are calculated both as:

(Average Signal−Average Noise)÷(Maximum Noise−Average Noise)

as well as:

(Average Signal−Average Noise)÷(3 $\sigma_{Noise}$).

TABLE 2

Typical Ultrasonic Signals and Noise Measurements in Ti6242 Blocks

| | | FBH Signals | | Noise | | | |
|---|---|---|---|---|---|---|---|
| Material | MHz | Attenuation dB | S | Attenuation dB | $N_{ave}$ | $N_{Max}$ | $\sigma_{noise}$ |
| Conventional billet | 6.62 | −34 | 94.4 | −12 | 61.3 | 141 | 11.1 |
| Conventional, forged | 6.62 | −34 | 53.4 | −12 | 44.7 | 107.5 | 9.48 |
| UFG billet | 6.62 | −34 | 216.1 | −12 | 9.1 | 34.5 | 1.70 |
| UFG, forged | 6.62 | −34 | 108.5 | −12 | 4.3 | 12.5 | 0.973 |
| Conventional billet | 11.36 | −49 | 75.4 | −12.5 | 130.9 | 243.5 | 21.5 |
| Conventional, forged | 11.36 | −49 | 42.7 | −12.5 | 81.8 | 249.5 | 17.2 |
| UFG billet | 11.36 | −49 | 214.5 | −12.5 | 23.1 | 59.5 | 4.38 |
| UFG, forged | 11.36 | −49 | 100.5 | −12.5 | 5.9 | 11.5 | 1.11 |
| Conventional billet | 18.43 | −48.5 | 51.3 | −10 | 73.6 | 168.5 | 12.4 |
| Conventional, forged | 18.43 | −48.5 | 20.4 | −10 | 38.8 | 142.5 | 8.35 |
| UFG billet | 18.43 | −48.5 | 212.2 | −10 | 21.5 | 71.5 | 4.11 |
| UFG, forged | 18.43 | −48.5 | 93.5 | −10 | 11.9 | 20.5 | 1.40 |

The determined signal to noise ratio calculations, as embodied by the invention, are listed in Table 3. Both calculation methods, as described above, provide a measure of a signal's intensity in a selected block relative to noise spikes in the same block.

TABLE 3

Signal to Noise Ratio in Ti6242 Blocks

| | | Signal to Noise Ratio | |
|---|---|---|---|
| Material | MHz | $(S_{ave}-N_{ave})/(N_{Max}-N_{ave})$ | $(S_{ave}-N_{ave})/3\sigma_{noise}$ |
| Conventional billet | 6.62 | 14.2 | 33.9 |
| Conventional, forged | 6.62 | 10.0 | 22.0 |
| UFG billet | 6.62 | 106.7 | 531.3 |
| UFG, forged | 6.62 | 166.6 | 466.4 |
| Conventional billet | 11.36 | 43.6 | 76.1 |
| Conventional, forged | 11.36 | 16.5 | 53.7 |
| UFG billet | 11.36 | 393.7 | 1089.8 |
| UFG, forged | 11.36 | 1195.2 | 2015.7 |
| Conventional billet | 18.43 | 44.7 | 113.8 |
| Conventional, forged | 18.43 | 16.2 | 67.0 |
| UFG billet | 18.43 | 356.7 | 1445.5 |
| UFG, forged | 18.43 | 915.0 | 1873.2 |

Accordingly, if the determining a signal to noise ratio level is conducted by Average Signal−Average Noise)÷(Maximum Noise−Average Noise), it can be generalized that the material comprises uniform fine grains at 6.62 MHz if the a signal to noise ratio—for a signal from 0.79 mm (1/32 inch) diameter flat bottom holes 25 mm below the inspected surface of the material—is at least about 20; at 11.36 MHz a signal to noise ratio level is at least about 50; and at 18.43 MHz a signal to noise ratio level is at least about 50. Further, if the determining a signal to noise ratio level is conducted (Average Signal−Average Noise)÷(3 $\sigma_{Noise}$) for the subject flat bottom holes, it can be also generalized that the material comprises uniform fine grains at 6.62 MHz if the a signal to noise ratio level is at least about 50; at 11.36 MHz a signal to noise ratio level is at least about 100; and at 18.43 MHz a signal to noise ratio level is at least about 150. Each of these signal to noise ratio levels correspond to a preset noise level as determined by the pre-drilled holes in the material.

Figure 6:
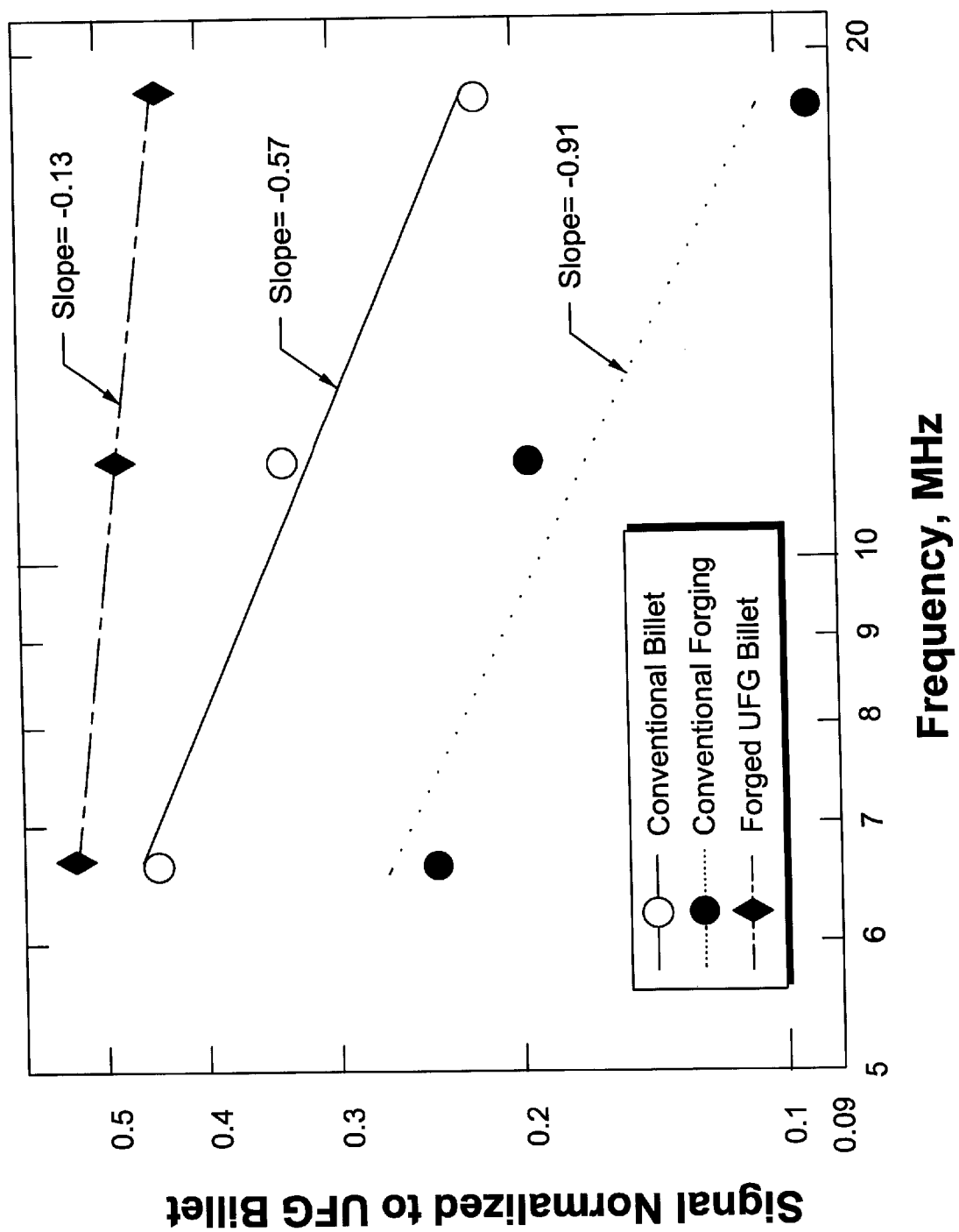
FIG. 6 illustrates a graph of the average signals from flat bottom holes with respect to those in the block machined from the conventional billet.
Figure 7:
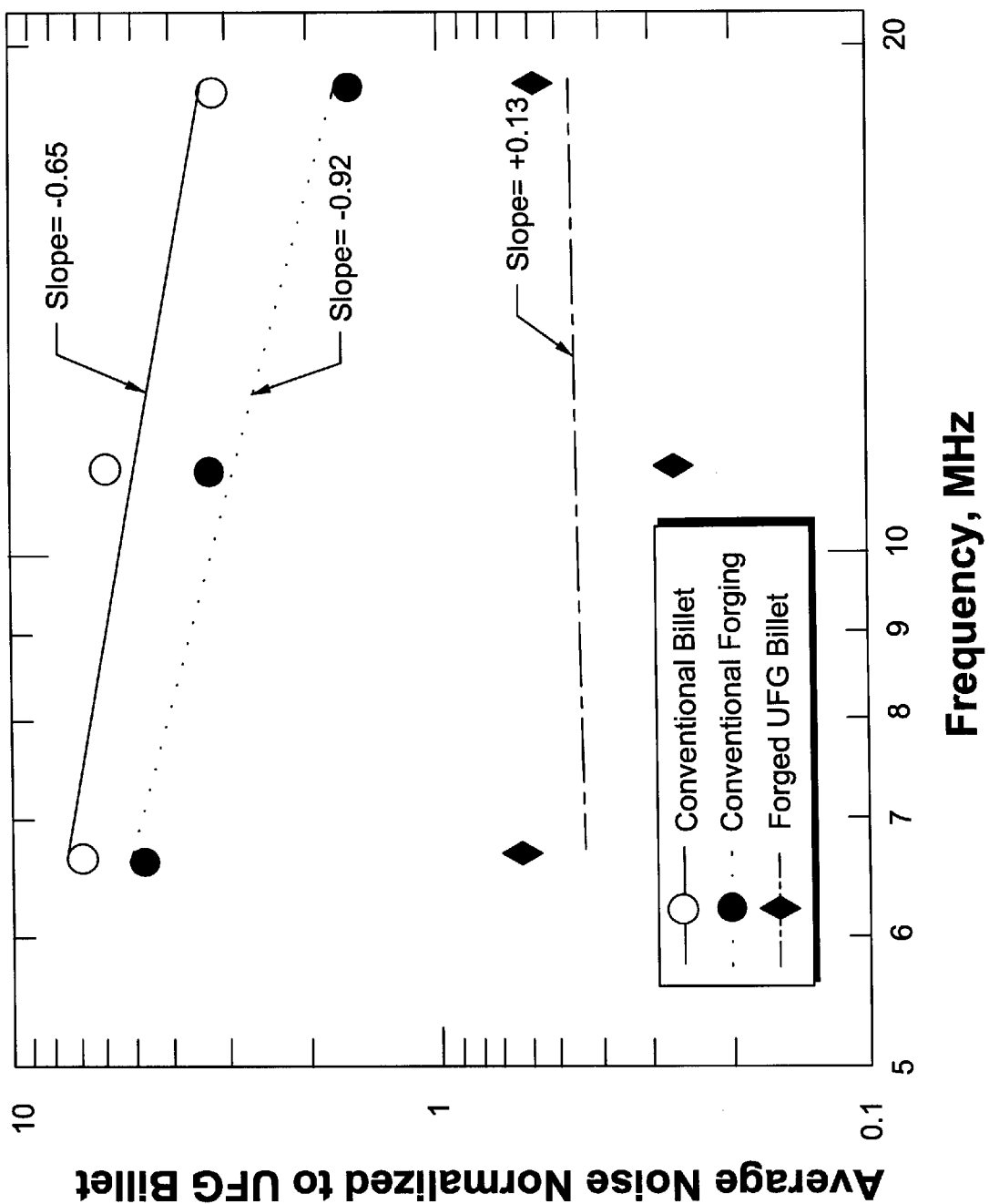
FIG. 7 illustrates a graph of average noise from blocks referenced to that from the block machined from the conventional billet.
Figure 8:
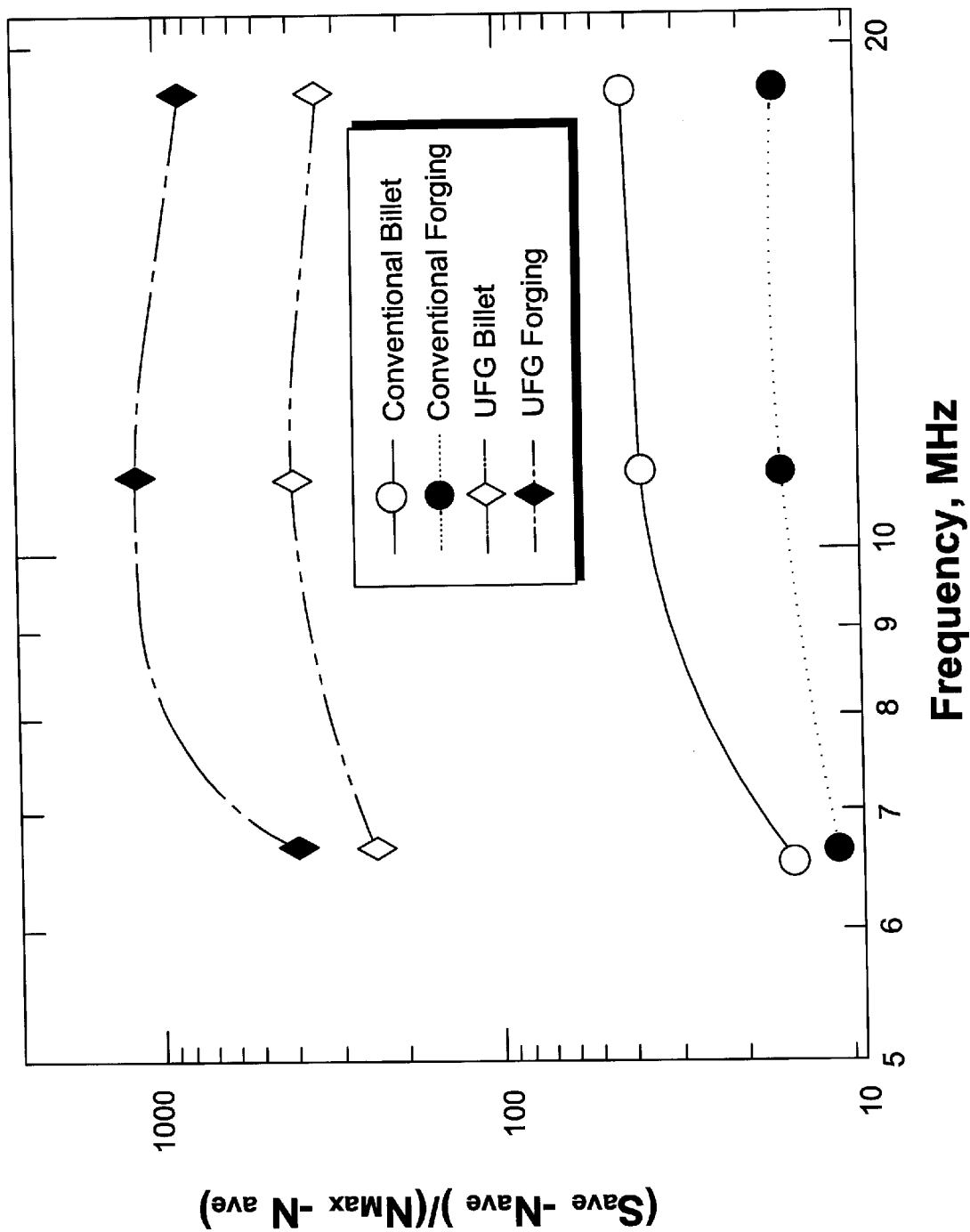
FIG. 8 illustrates a graph of signal to noise ratios of Ti6242 blocks as a function of frequency.

The highest signal from flat bottom holes is measured in the UFG billet, and the lowest signal from flat bottom holes is measured in a conventional forging, as illustrated in the graph of FIG. 6. The highest average noise, the largest maximum noise, and the largest standard deviation of noise are measured in a conventional billet. The lowest average noise, the smallest maximum noise, and the smallest standard deviation of noise are measured in a forging of UFG material, as illustrated in the graph of FIG. 7. Accordingly, it can be determined that the forged UFG material possesses the highest signal to noise ratio, and that the conventional forging had the lowest signal to noise ratio, as illustrated in the graph of FIG. 8.

In the ultrasonic inspection, as embodied by the invention, longitudinal sound velocities were measured in a Ti6242 extrusion. The Ti6242 extrusion was processed to create a strong [0001] texture in the direction of extrusion. For example, the extrusion of the Ti6242 is performed at about 1040° C. and a ratio of about 8:1. The extrusion is then heat treated at about 593° C. for about 8 hours. X-ray investigation and analysis determine the grain and microstructure orientation of the Ti6242. This investigation and analysis of the Ti6242 indicates a strong [0001] texture along the extrusion direction, with [0001] intensity along the extrusion direction. The intensity has been determined to be about 22 times random.

The ultrasonic behavior of small blocks of a titanium alloy, for example a Ti6242 alloy, can be determined by ultrasonic inspection as a function of ultrasonic frequency and material microstructure. The speed of sound in $\alpha$Ti is about 6 mm/$\mu$s. At an ultrasonic frequency of 5 MHz, the wavelength is about 1.2 mm. Colony sizes greater than about 200 $\mu$m could change the scattering character from Rayleigh toward stochastic (phase). Sound velocities in the Ti6242 are measured on rectangular Ti6242 pieces that are formed from the respective Ti6242 billets. The rectangular Ti6242 pieces are about 16 mm long in the extrusion direction and about 12 mm in length in a direction normal to the extrusion direction. Longitudinal velocity is measured at about 10 MHz with a contact transducer, amplifier, and oscilloscope. The longitudinal velocity is determined by measuring a time for a sound pulse to travel down the selected direction and return. The sound velocity along the extrusion direction is about 6.28 mm/$\mu$s; while the sound velocity in a direction normal to the extrusion direction is about 6.10 mm/$\mu$s.

The results from the ultrasonic inspection and the determination of the titanium-containing materials, along with microstructure characteristic are based on UFG billet blocks, which are formed from conventional billet material, as described above. The UFG process produces samples in which the original $\alpha$Ti colony structure in the conventional billet is eliminated. The steps of forging the UFG material at about 900° C. and with a corresponding about a 60% height reduction did not re-create $\alpha$Ti colonies or develop strong texture and $\alpha$Ti microstructure.

Figure 5:
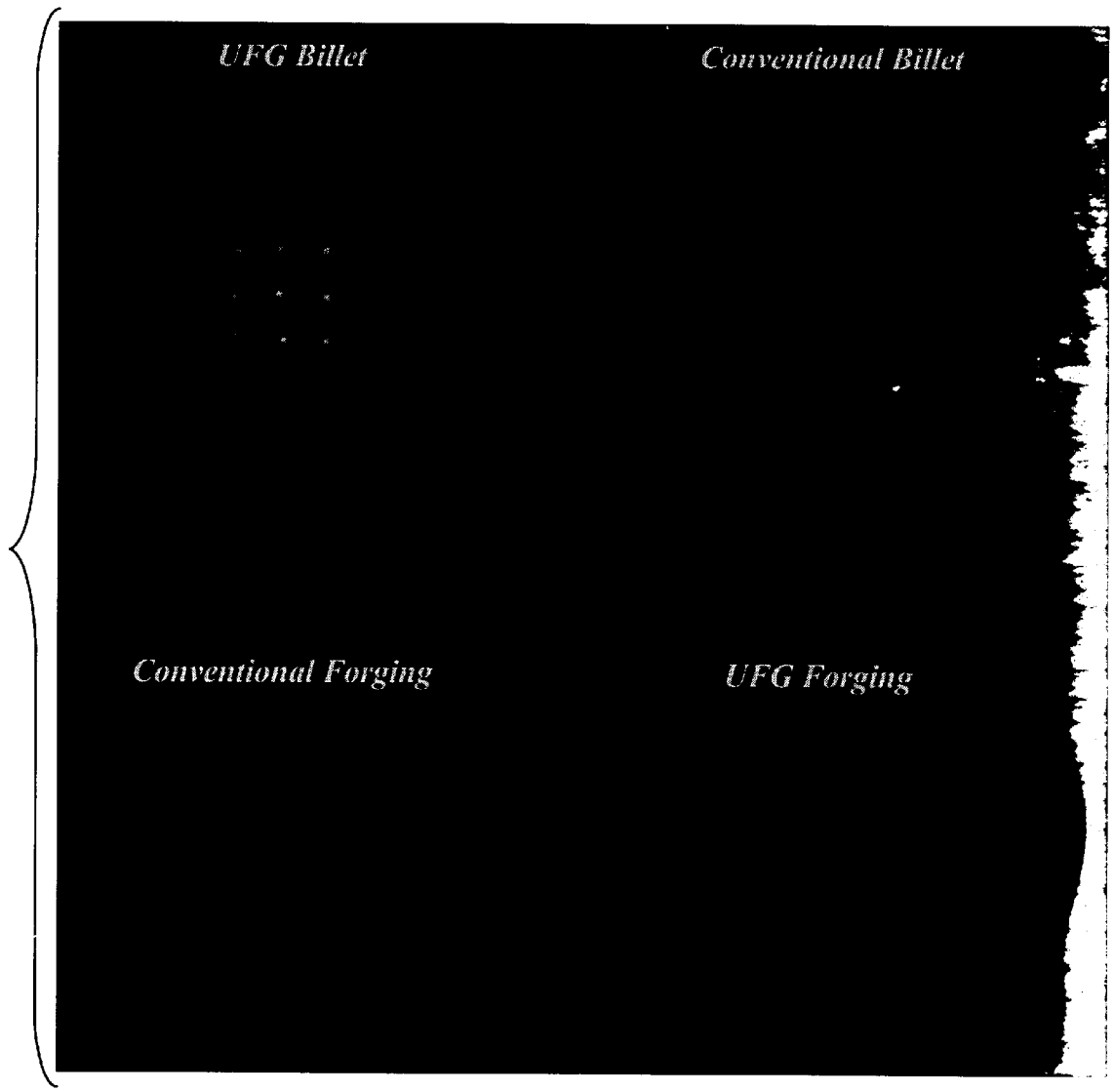
FIG. 5 illustrate 5 MHz C-scan images of Ti6242 blocks containing arrays of 0.79 mm (1/32 inch) diameter flat bottom holes, which are drilled 25 mm below a surface, in which the top left is titanium UFG billet, the top right is a conventional titanium billet, the bottom left is a conventional titanium forging, and the bottom right is a titanium UFG forging, wherein the 5 MHz C-scan images are taken at 34 dB attenuation signal scan.

With reference to FIGS. 6 and 7, differences in sound scattering sensitivity and noise are illustrated to be generally dependent on frequency. This dependency suggests that a scattering entity size, such as the size of a colony, in the conventional material increases the contribution to scattering, sound scattering sensitivity, and attenuation from phase scattering. This change in contribution is not a complete shift from one pure scattering mechanism to the other scattering mechanism, such as a Rayleigh scattering mechanism to a phase scattering mechanism, since such a shift would give a slope of about −2 in FIG. 5.

The $\alpha$Ti particle size alone is generally not significant in any determining of a signal to noise ratio, since the $\alpha$Ti particle sizes are similar in all materials and are generally smaller in size than the ultrasonic wavelength. A difference in the various material, in the ultrasonic inspection, as embodied by the invention, comprises the presence of large colonies in conventional billets and forgings. Noting this difference, the speed of sound in Ti6242 extrusion samples is about 6 mm/$\mu$s. This speed typically corresponds to ultrasonic inspection wavelengths of about 1.2 mm at about 5 MHz, about 600 $\mu$m at about 10 MHz, and about 300 $\mu$m at about 20 MHz. Therefore, the colony dimensions in the conventional billet and forging are comparable to the ultrasonic wavelength.

The relative contributions of Rayleigh scattering and phase scattering are frequency dependent, for example in the ultrasonic frequency range. The frequency dependency is due, at least in part, to the 18.43 MHz wavelength of about 300 $\mu$m being about the size of a $\alpha$Ti colony thickness. The 6.62 MHz wavelength of about 900 $\mu$m is about 3 times a $\alpha$Ti colony size. Scattering at 6.62 MHz enters the phase scattering region for its contribution, while scattering at 18.43 MHz provides substantial phase scattering contributions.

The UFG forged material results in a slightly larger grain size than the original billet. However, UFG forged material possesses a lower noise and higher signal, as indicated in Table 2. This behavior may be due to a slightly lower volume fraction of $\alpha$Ti particles in the forged material, which is illustrated in FIG. 1, legends (c) and (d).

The conventional forging possesses a lower noise than a conventional billet, however, it has a lower signal to noise ratio, which may be due in part to low signals from the flat bottom holes. The conventional forging has a lower volume fraction of $\alpha$Ti particles than the billet. The lower signal in the conventional forging may be caused by attenuation due, at least in part, to sound traveling along highly textured regions. The dimensions of the reflecting entity $\alpha$Ti colonies up to about 1 mm in length and about 300 $\mu$m in width in the conventional billet and forging may result in a stochastic (phase) component to the resultant scattering. It is also possible that a $\alpha$Ti colony structure above the flat bottom holes scatters the reflection from the flat bottom holes.

The microstructures of UFG billets and forgings made from UFG billets comprise fine-scale granular $\alpha$Ti particles. These $\alpha$Ti particles are generally less than about 5 $\mu$m in diameter, and are generally provided with an absence of crystallographic texture. Ultrasonic inspectability, which is characterized by signal to noise ratio from machined flat bottom holes, is greater in the UFG materials than in the conventional materials. There is less ultrasonic backscattered noise in the UFG materials than there is in the conventional materials. Further, the ultrasonic signal from machined flat bottomed holes is higher in the UFG material.

The presence of $\alpha$Ti colony structure is associated with ultrasonic noise generated by ultrasonic inspection, as embodied by the invention. For materials with $\alpha$Ti particles less than about 10 $\mu$m in size, differences in $\alpha$Ti particle size typically do not have a significant effect on generated ultrasonic noise. For example, UFG billets, as embodied by the invention, display chiefly Rayleigh scattering, while conventional billets, which can not be characterized by UFG properties, display Rayleigh scattering plus phase scattering. The inspectability of titanium-containing materials is enhanced with predominantly Rayleigh scattering.

While various embodiments are described herein, it will be appreciated from the specification that various combinations of elements, variations or improvements therein may be made by those skilled in the art, and are within the scope of the invention.

What is claimed is:

1. An ultrasonic inspection method for determining acceptability of material for microstructurally sensitive applications, the method comprises:
   providing a material,
   directing ultrasonic energy for ultrasonic inspection into the bulk of the material;
   scattering reflected energy in the bulk of the material;
   determining an amount of noise generated by the ultrasonic inspection; and
   characterizing the material as acceptable if the amount of noise as a function of ultrasonic frequency or wavelength is characteristic of predominantly Rayleigh scattering and the magnitude of the noise is less than a pre-determined noise level.

2. A method according to claim 1, wherein the step of providing a material comprises providing a titanium material, and the step of characterizing comprises characterizing that the titanium is acceptable for microstructurally sensitive applications.

3. A method according to claim 2, wherein the step of characterizing the titanium material as acceptable comprises relating the determined amount of noise to an amount of scattering generated by the step of directing.

4. A method according to claim 3, wherein the step of characterizing the titanium material as acceptable if the amount of noise corresponds to a preset noise level comprises determining if the noise corresponds to scattering that comprises predominantly Rayleigh scattering.

5. A method according to claim 4, wherein if the step of determining if the scattering comprises predominantly Rayleigh scattering comprises determining predominantly Rayleigh scattering, the step of characterizing comprises characterizing the titanium material as acceptable for microstructurally sensitive titanium applications.

6. A method according to claim 4, wherein if the step of determining if the scattering comprises predominantly Rayleigh scattering comprises determining Rayleigh scattering and other scattering, the step of characterizing comprises characterizing the titanium material as not acceptable for microstructurally sensitive titanium applications.

7. A method according to claim 2, wherein the step of providing the material comprises:
   providing at least one of: a billet; a forging; a billet treated to comprise uniform fine grains; and a forged billet treated to comprise uniform fine grains.

8. A method according to claim 7, wherein the step of providing a billet comprises providing a billet that comprises αTi particles, the αTi particles being arranged in αTi colonies, the αTi colonies being larger than about ¼ the wavelength of the ultrasound selected for inspection.

9. A method according to claim 7, wherein the step of providing a forging comprises providing a forging that comprises αTi particles, the αTi particles being arranged in αTi colonies, the αTi colonies being larger than about ¼ the wavelength of the ultrasound selected for inspection.

10. A method according to claim 7, wherein the step of providing a billet treated to comprise uniform fine grains comprises providing a billet treated to comprise uniform fine grains in which the treated billet comprises αTi particles having diameters about 5 μm, and the αTi phase crystallographic orientation being random.

11. A method according to claim 7, wherein the step of providing a forged billet treated to comprise uniform fine grains comprises providing forged billet treated to comprise uniform fine grains in which the treated billet comprises αTi particles, the αTi particles have diameters about 10 μm, and suggesting grain growth during at least one of the forging or heat treatment steps, and αTi phase crystallographic orientation being random.

12. A method according to claim 2, wherein the step of determining an amount of noise generated comprises determining a signal to noise ratio and the step of characterizing comprises determining that the signal to noise ratio is above a certain preset signal to noise ratio level.

13. A method according to claim 12, the step of providing the material comprises providing a material with at least one flat bottom hole target formed therein, and the step of scattering energy in the material comprises scattering energy at the at least one target and at other locations in the material.

14. A method according to claim 13, wherein the step of directing ultrasonic energy in the material for ultrasonic inspection comprises:
   ultrasonic inspection by water immersion ultrasonic C-scanning processing titanium materials, the water immersion ultrasonic C-scans comprising:
   obtaining first set of C-scans at nominal frequencies of about 5 MHz, about 10 MHz, and 20 MHz to measure a signal from the flat bottom holes;
   obtaining a second set of C-scans at an amplification greater than that of the first set of C-scans;
   obtaining C-scan images for each C-scan;
   quantitatively determining signal and noise for each C-scan, in which the signal from the at least one flat bottom hole comprises the brightest pixel for each C-scan due to reflection from the flat bottom hole;
   determining noise statistics and sound scattering sensitivity;
   determining a signal to noise ratio level by at least one of:

(Average Signal−Average Noise)÷(Maximum Noise−Average Noise);

or (Average Signal−Average Noise)÷(3 $\sigma_{Noise}$), where $\sigma_{Noise}$ is the standard deviation for determined noise from each C-scan.

15. A method according to claim 14, wherein the step of determining a signal to noise ratio level comprises:
   determining that the titanium material comprises uniform fine grains by measuring (Average Signal−Average Noise)÷(Maximum Noise−Average Noise) from 0.79 mm (¹⁄₃₂ inch) flat bottom holes located 25 mm below the surface being inspected and determining that the material comprises uniform fine grains if at about 6.6 MHz the signal to noise ratio is at least about 20; at about 11 MHz the signal to noise ratio is at least about 50; and at about 18 MHz the signal to noise ratio is at least about 50.

16. A method according to claim 14, wherein the step of determining a signal to noise ratio level comprises:
   determining that the titanium material comprises uniform fine grains level by (Average Signal−Average Noise)÷(3 $\sigma_{Noise}$) from 0.79 mm (¹⁄₃₂ inch) flat bottom holes located 25 mm below the surface being inspected and determining that the material comprises uniform fine grains if at about 6.6 MHz the signal to noise ratio is at least about 50; at about 11 MHz the signal to noise ratio is at least about 100; and at about 18 MHz the signal to noise ratio is at least about 150.

17. An ultrasonic inspection method for determining acceptability of a titanium material for microstructurally sensitive applications, the method comprising:

providing a titanium material;

directing ultrasonic energy of ultrasonic inspection to the material; and scattering reflected energy in the material; and determining an amount of noise generated by the ultrasonic inspection; and characterizing the titanium material is acceptable for microstructurally sensitive applications if the amount of noise corresponds to a preset noise level, wherein the step of characterizing the titanium material as acceptable comprises relating the determined amount of noise to an amount of scattering generated by the step of directing, and characterizing the titanium material as acceptable if the amount of noise corresponds to a preset noise level comprises determining if the noise corresponds to scattering that comprises predominantly Rayleigh scattering, wherein the step of determining an amount of noise generated comprises determining a signal to noise ratio and the step of characterizing comprises determining that the signal to noise ratio is above a certain preset signal to noise ratio level, and the step of providing the material comprises providing a material with at least one flat bottom hole target formed therein, and the step of scattering energy in the material comprises scattering energy at the target and at other locations in the material, further wherein the step of directing ultrasonic energy in the material for ultrasonic inspection comprises:

ultrasonic inspection by water immersion ultrasonic C-scanning processing titanium materials, the water immersion ultrasonic C-scans comprising:

obtaining first set of C-scans at more than one frequency to measure a signal from the target;

obtaining a second set of C-scans at amplification greater than that of the first set of C-scans;

quantitatively determining signal and noise for each C-scan, in which the signal from the at least one target comprises a measure of signal from the target, as the brightest pixel for each C-scan from the target;

determining noise statistics and sound scattering sensitivity;

determining a signal to noise ratio level by:

(Average Signal–Average Noise)÷(Maximum Noise–Average Noise);

or (Average Signal–Average Noise)÷($3\sigma_{Noise}$), where $\sigma_{Noise}$ is the standard deviation for determined noise from each C-scan.

18. An ultrasonic inspection system for determining acceptability of material for microstructurally sensitive applications, the system comprising:

means for providing a material, means for directing ultrasonic energy for ultrasonic inspection into the bulk of the material;

means for scattering reflected energy in the bulk of the material;

means for determining an amount of noise generated by the ultrasonic inspection; and means for characterizing the material as acceptable if the amount of noise corresponds to a preset noise level.

19. A system according to claim 18, wherein the means for providing a material comprises providing a titanium material, and the means for characterizing comprises characterizing that the titanium is acceptable for microstructurally sensitive applications.

20. A system according to claim 19, wherein the means for characterizing the titanium material as acceptable comprises means for relating the determined amount of noise to an amount of scattering generated by the means for directing.

21. A system according to claim 20, wherein the means for characterizing the titanium material as acceptable if the amount of noise corresponds to a preset noise level comprises means for determining if the noise corresponds to scattering that comprises predominantly Rayleigh scattering.

22. A system according to claim 21, wherein if the means for determining if the scattering comprises predominantly Rayleigh scattering determines predominantly Rayleigh scattering, the means for characterizing characterizes the titanium material as acceptable for microstructurally sensitive titanium applications.

23. A system according to claim 22, wherein if the means for determining if the scattering comprises predominantly Rayleigh scattering determines Rayleigh scattering and other scattering, the means for characterizing characterizes the titanium material as not acceptable for microstructurally sensitive titanium applications.

24. A system according to claim 19, wherein the means for providing the material comprises:

means for providing at least one of: a billet; a forging; a billet treated to comprise uniform fine grains; and a forged billet treated to comprise uniform fine grains.

25. A system according to claim 24, wherein the means for providing a billet comprises means for providing a billet that comprises αTi particles, the αTi plates being arranged in αTi colonies, the αTi colonies having dimensions greater than about ¼ the wavelength of the sound used for inspection.

26. A system according to claim 24, wherein the means for providing a forging comprises means for providing a forging that comprises αTi particles particles, the αTi having maximum dimension about 10 μm, the αTi plates being arranged in αTi colonies, the αTi colony having dimensions greater than about ¼ the wavelength of the sound used for inspection.

27. A system according to claim 24, wherein the means for providing a billet treated to comprise uniform fine grains comprises means for providing a billet treated to comprise uniform fine grains in which the treated billet comprises αTi particles having diameters about 5 μm, and the αTi phase crystallographic orientation being random.

28. A system according to claim 24, wherein the means for providing a forged billet treated to comprise uniform fine grains comprises means for providing forged billet treated to comprise uniform fine grains in which the treated billet comprises αTi particles, the αTi particles have diameters about 10 μm, and suggesting grain growth during at least one of forging or heat treatment, and αTi phase crystallographic orientation being random.

29. A system according to claim 19, wherein the means for determining an amount of noise generated comprises means for determining a signal to noise ratio and the means for characterizing comprises determining that the signal to noise ratio is above a certain preset signal to noise ratio level.

30. A system according to claim 29, the means for providing the material comprises means for providing a material with at least one flat bottom target hole formed therein, and the means for scattering energy in the material comprises scattering energy at the at least one target and at other locations in the material.

31. A system according to claim 30, wherein the means for directing ultrasonic energy in the material for ultrasonic inspection comprises:
  means for ultrasonic inspection by water immersion ultrasonic C-scanning processing titanium materials, the water immersion ultrasonic C-scans comprising:
  means for obtaining first set of C-scans at more than one frequency to measure a signal from targets, such as flat bottom holes;
  means for obtaining a second set of C-scans at amplification greater than that of the first set of C-scans;
  means for quantitatively determining signal and noise for each C-scan, in which the signal from the at least one target is determined by some measure of the amount of reflected energy, such the value of brightest pixel associated with the target for each C-scan;
  means for determining noise statistics and sound scattering sensitivity;
  means for determining a signal to noise ratio level such as by:

(Average Signal−Average Noise)÷(Maximum Noise−Average Noise);

or (Average Signal−Average Noise)÷(3 $\sigma_{Noise}$), where $\sigma_{Noise}$ is the standard deviation for determined noise from each C-scan.

32. An ultrasonic inspection system for determining acceptability of a titanium material for microstructurally sensitive applications, the system comprising:
  means for providing a titanium material;
  means for directing ultrasonic energy of ultrasonic inspection to the bulk of the material; and
  means for scattering reflected energy in the material; and
  means for determining an amount of noise generated by the ultrasonic inspection; and
  means for characterizing the titanium material is acceptable for microstructurally sensitive applications if the amount of noise corresponds to a preset noise level, wherein the means for characterizing the titanium material as acceptable comprises means for relating the determined amount of noise to an amount of scattering generated by the means for directing, and means for characterizing the titanium material as acceptable if the amount of noise corresponds to a preset noise level comprises means for determining if the noise corresponds to scattering that comprises predominantly Rayleigh scattering,
  wherein the means for determining an amount of noise generated comprises means for determining a signal to noise ratio and the means for characterizing comprises determining that the signal to noise ratio is above a certain preset signal to noise ratio level, and the means for providing the material comprises providing a material with at least one target, such as flat bottom hole formed therein, and the means for scattering energy in the material comprises scattering energy at the at least target and at other locations in the material, further wherein the means for directing ultrasonic energy in the material for ultrasonic inspection comprises:
    means for ultrasonic inspection by water immersion ultrasonic C-scanning processing titanium materials, the water immersion ultrasonic C-scans comprising:
    means for obtaining first set of C-scans more than one frequency to measure a signal from the flat bottom holes;
    means for obtaining a second set of C-scans at amplification greater than that of the first set of C-scans;
    means for quantitatively determining signal and noise for each C-scan, in which the signal from the at least at least one target is determined by some measure of the amount of reflected energy, such the value of brightest pixel associated with the target for each C-scan;
    means for determining noise statistics and sound scattering sensitivity; means for determining a signal to noise ratio level such as by:

(Average Signal−Average Noise)÷(Maximum Noise−Average Noise);

or (Average Signal−Average Noise)÷(3 $\sigma_{Noise}$), where $\sigma_{Noise}$ is the standard deviation for determined noise from each C-scan.

* * * * *